United States Patent [19]
Brossmer et al.

[11] Patent Number: 6,140,543
[45] Date of Patent: Oct. 31, 2000

[54] PROCESS FOR THE PRODUCTION OF 1,3-PROPANEDIOL

[75] Inventors: Christoph Brossmer, Frankfurt, Germany; Dietrich Arntz, Mobile, Ala.

[73] Assignee: E. I. du Pont de Nemours and Company, Wilmington, Del.

[21] Appl. No.: 09/016,444

[22] Filed: Jan. 30, 1998

[30] Foreign Application Priority Data

Jan. 30, 1997 [DE] Germany ............................ 197 03 383

[51] Int. Cl.$^7$ .......................... C07C 27/04; C07C 45/00; C08F 5/20; C08G 5/20
[52] U.S. Cl. ............................ 568/458; 568/862; 521/32; 521/36
[58] Field of Search .................... 568/862, 458; 521/32, 36

[56] References Cited

U.S. PATENT DOCUMENTS

| | | | |
|---|---|---|---|
| 3,536,763 | 10/1970 | Eleuterio | 568/458 |
| 5,015,789 | 5/1991 | Arntz | 568/862 |
| 5,171,898 | 12/1992 | Arntz | 568/862 |
| 5,414,020 | 5/1995 | Heller | 521/32 |

FOREIGN PATENT DOCUMENTS

| | | |
|---|---|---|
| 0 412 337 A2 | 2/1991 | European Pat. Off. . |
| 0 464 458 A1 | 1/1992 | European Pat. Off. . |
| 0 487 903 A2 | 6/1992 | European Pat. Off. . |
| 0 713 853 A1 | 5/1996 | European Pat. Off. . |
| 40 38 192 | 6/1992 | Germany . |

OTHER PUBLICATIONS

XP–002063242, Chemical Abstracts, "Synthesis and Properties of Ampholyte–Supports", vol. 96, No. 23 (Jun. 7, 1982), Abstract 199037c, p. 612.

XP–002061949, Chemical Abstracts, "Synthesis and Characterization of Polyacrylamide–acrylic Acid Resin and its Use for Treatment of Radioactive Liquid Waste", vol. 123, No. 26 (Dec. 25, 1995), Abstract 352823d.

XP–002063243, Chemical Abstracts, "Facilitated Transport of Carbon Dioxide Through Functional membranes Prepared by Plasma Graft Polymerization Using Amines as Carrier", vol. 125, No. 22 (Nov. 25, 1996), Abstract 279588r, p. 235.

XP–002061840, Database WPI, Week 9632, Derwent Publications Ltd., London, GB; Preparation of Hydroxyalkanal by Hydrated Unsaturated Aldehyde Presence Carboxylic Acid; (Jun. 4, 1996).

*Primary Examiner*—Gary Geist
*Assistant Examiner*—Everett White

[57] ABSTRACT

A process for the production of 1,3-propanediol by hydrating acrolein in the presence of an ion exchanger to form 3-hydroxypropionaldehyde includes reacting acrolein and water in a ratio by weight of 1:2 to 1:20 at 30° to 120° C. and a pressure in the range from 1 to 20 bar, in the presence of an ion exchange hydration catalyst. The ion exchanger and any unreacted acrolein are separated from the reaction mixture. The 3-hydroxypropionaldehyde is then catalytically hydrogenated in a liquid or gas phase using hydrogenation catalysts. The ion exchanger hydration catalyst includes polyamine/polycarboxylic acid resins produced by reacting polyamine resins based on a crosslinked polyacrylamide matrix with acrylic acid, acrylic acid derivatives or a salt of an ω-haloalkanoic acid. An ion exchanger includes reaction product of reacting a polyamine resin based on a crosslinked polyacrylamide matrix with acrylic acid, acrylic acid derivatives or ω-haloalkanoic acid salts.

5 Claims, No Drawings

PROCESS FOR THE PRODUCTION OF 1,3-PROPANEDIOL

CROSS-REFERENCE TO RELATED APPLICATION

This application claims priority from German Application No. 197 03 383.0 filed on Jan. 30, 1997, the subject matter of which is hereby incorporated herein by reference.

FIELD OF THE INVENTION

This invention relates to a process for the production of 1,3-propanediol by hydrating acrolein in the presence of an ion exchange resin with subsequent catalytic hydrogenation of the 3-hydroxypropionaldehyde.

BACKGROUND OF THE INVENTION 1,3-Propanediol has many applications as a monomer unit for polyester and polyurethanes and as a starting material for the synthesis of cyclic compounds.

It is known to produce 1,3-propanediol by hydrating acrolein to yield 3-hydroxypropionaldehyde and then hydrogenating to yield 1,3-propanediol.

According to U.S. Pat. No. 2,434,110, acrolein may be hydrated in the presence of an acidic catalyst, wherein 3 hydroxypropionaldehyde is formed. The reaction proceeds at elevated temperature using a 5 to 30 wt. % solution of acrolein in water and an acid or acidic salts as the catalyst. The reaction mixture obtained from hydration, optionally after removal of unreacted acrolein, is hydrogenated in the presence of known hydrogenation catalysts. Suitable catalysts for hydrogenating 3-hydroxypropionaldehyde to 1,3-propanediol are those containing one or more metals having a hydrogenating action, such as, for example, Fe, Co, Ni, Cu, Ag, Mo, W, V, Cr, Rh, Pd, Os, Ir or Pt.

One disadvantage of the known process according to U.S. Pat. No. 2,434,110 is the low yield of 1,3-propanediol, which is in particular attributable to secondary reactions which consume acrolein during the hydration stage. The selectivity of the mineral acid-catalyzed hydration is moreover strongly dependent on acrolein conversion.

In order to achieve acceptable selectivity, hydration is terminated at a low acrolein conversion, wherein, however, only a low space-time yield is achievable.

Attempts to remedy the disadvantages of the process are known. It has thus been attempted to obtain carboxylic acid esters of 3-hydroxypropionaldehyde by attaching lower carboxylic acids to acrolein with heating (U.S. Pat. No. 2,638, 479) or in the presence of a basic ion exchange resin, which esters may be hydrogenated to yield the corresponding 1,3-propanediol esters. Disadvantages of these processes include the additional steps required to saponify the ester and to recycle the carboxylic acid and the unwanted formation of n-propanol and the carboxylic acid esters thereof during hydrogenation (DB-OS 20 57 399). It is also known to hydrate acrolein with carbon dioxide as the catalyst, but this process requires long reaction times (DE-OS 19 05 823).

It has been found that while acrolein may be hydrated using phosphoric acid or dihydrogen phosphates as the catalyst, problems occur during the subsequent hydrogenation if the resultant hydroxypropionaldehyde solution is hydrogenated without careful separation of the hydration catalyst (EP-A 0 487 903).

When per se highly active nickel hydrogenation catalysts are used, the catalyst is more rapidly deactivated on repeated use than when a reaction mixture containing neither acid nor salt is hydrogenated. This results in increased catalyst consumption. Furthermore, the presence of the hydration catalyst during working up by distillation causes product losses due to decomposition or, in the case of preceding neutralization, to blockages and encrustation in the plant. It is also more difficult and thus more expensive to dispose of distillation residues if they contain inorganic salts than if they do not (EP-A 0 487 903).

The disadvantages may in part be avoided if the hydration catalyst is removed from the reaction mixture by means of ion exchangers before the hydrogenation or if the 3-hydroxypropionaldehyde is extracted from the reaction mixture and then hydrogenated. However, both alternative measures for reducing consumption of the costly hydrogenation catalyst entail additional equipment. They result in higher energy consumption and waste water problems, thus increasing the production costs for 1,3-propanediol (EP-A 0 487 903).

According to U.S. Pat. No. 3,536,763, acrolein is hydrated at 40° to 120° C. in the presence of weakly acidic cation exchange resins, the functional groups of which are solely carboxyl groups. 3-Hydroxypropionaldehyde yields are stated to be approximately 80%, wherein yields are apparently virtually independent of acrolein conversion in the range from 25 to 65%. This document also comprises the per se known hydrogenation of 3-hydroxypropionaldehyde to yield 1,3-propanediol.

While replication of the process of U.S. Pat. No. 3,536, 763 did indeed allow the catalytic activity of the ion exchange resins containing carboxyl groups to be confirmed, the degree of activity did not seem suitable for use of these ion exchangers in an industrial plant. It has in fact been found that these catalysts require relatively high temperatures and relatively long reaction times, which runs contrary to the desired elevated space-time-yield and elevated selectivity.

It is furthermore known to perform hydration for the production of 1,3-propanediol in the presence of a chelating ion exchanger (EP-A 0 487 903).

Using chelating ion exchangers has the disadvantage that these resins are subject to unwanted changes in volume/shrinkage of up to 45% on conversion from the standard commercial Na form into the catalytically active H form ("activation"), which causes problems for industrial use and results in long catalyst changing times. A further disadvantage is the sometimes low loading density with catalytically active, chelating anchor groups (for example of the iminodiacetic acid type), which results in a low (limited) total capacity (meq $H^+$/ml) of the resin. This latter parameter significantly affects the catalytic activity of the resins.

It is furthermore known, in connection with 1,3-propanediol production, to hydrate acrolein to produce 3-hydroxypropionaldehyde in the presence of cation exchange resins which contain phosphonic acid groups (EP-A 0 412 337).

Using cation exchange resins containing phosphonic acid groups has the disadvantage that, when the long-term test according to EP-A 0 412 337 is exactly replicated, these resins exhibit a lower selectivity and give rise to more secondary products than the chelating ion exchangers listed in EP-A 0 487 903. The activity of these resins is furthermore associated with unwanted shrinkage, which causes technical problems and extended catalyst changing times.

SUMMARY OF THE INVENTION

One object of the present invention is accordingly to provide an improved process for the production of 1,3- propanediol by hydrating acrolein in the presence of ion exchange resins with subsequent catalytic hydrogenation, the hydration stage of which process may be performed with good selectivity and the highest possible space-time yield.

A further object is to provide ion exchange catalysts for the purpose of acrolein hydration which do not exhibit the above-stated disadvantages of the above-mentioned resins and which have an elevated total capacity.

The reaction mixture obtained from hydration should also deactivate the hydrogenation catalyst as little as possible in order to allow the hydrogenation catalyst to be reused for subsequent batches, or to extend the service life of a fixed bed hydrogenation catalyst and thus to improve the economic viability of the process.

The present invention provides a process for the production of 1,3-propanediol by hydrating acrolein in the presence of an ion exchanger to form 3-hydroxypropionaldehyde, wherein acrolein and water are reacted in a ratio by weight of 1:2 to 1:20 at 30° to 120° C. and a pressure in the range from 1 to 20 bar, separating the ion exchanger and, if present, the unreacted acrolein from the reaction mixture and then catalytically hydrogenating the 3-hydroxypropionaldehyde under per se known conditions in the liquid or gas phase using conventional hydrogenation catalysts, which process is characterized in that polyamine resins based on a crosslinked polyacrylamide matrix are reacted with acrylic acid, acrylic acid derivatives or the salt of an ω-haloalkanoic acid and the resultant polyamine/polycarboxylic acid resins are used as the hydration catalyst.

The anion exchanger Lewatit E304/88 is offered for sale by Bayer AG for the selective removal of sulphates. This exchanger is a polyamine resin on a crosslinked polyacrylamide matrix. According to Bayer AG, it is produced by reacting a polyacrylate precursor (for example polyacrylic acid ester) with tetraethylenepentamine or triethylenetetramine. In this reaction, one of the amino groups forms an amide bond for attachment to the polyacrylate matrix. The remaining amino groups are free and determine the polyamine functionality of the resin.

The polyamine resin is initially unsuitable for hydrating acrolein because it is in the OH or Cl form as an anion exchanger and, under these conditions, only catalyzes the unwanted polymerization of acrolein. However, resins modified with a carboxylic acid or derivative thereof or salt thereof and exhibiting elevated H+ capacities are obtained by reaction with, for example, acrylic acid, acrylic acid derivatives or the salt of an ω-haloalkanoic acid (sodium 2-chloroacetate, Na 3-bromopropionate). The polyamine/polycarboxylic acid resins according to the invention are synthesized in accordance with the following schematic equations wherein, for the sake of clarity, the reaction is shown on only one amino group:

Reaction with Acrylic Acid

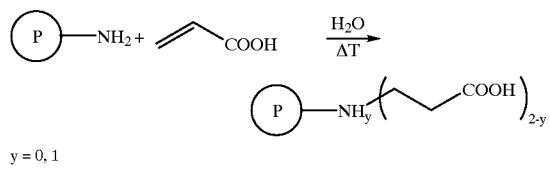

y = 0, 1

Reaction with an ω-halocarboxylic Acid Salt

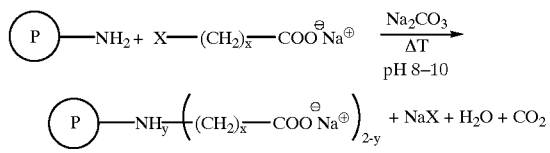

X = Cl, Br
x = 1–6
y = 0, 1

X=Cl, Br
x=1–6
y=0,1

In the first case, amino groups are added to the double bond of the acrylic acid or the derivative thereof, wherein amino- or iminodipropionic acid groups are produced. In the second case, amino- or iminodicarboxylic acids of variable chain length may be synthesized by condensation (elimination of HX). A characteristic feature of these derivatizations is the reversal of the polarity of the resin, i.e. the anion exchanger is converted into a cation exchanger.

The temperature used according to the invention for resin derivatization is 0°–150° C., preferably 20°–130° C. in the reaction with acrylic acid. Acrylic acid/methacrylic acid is used in stabilized form in the absence or presence of water. If the reaction is performed in an acid/water mixture, the acrylic/methacrylic acid content may be between 5 and 100 wt. %, preferably 30–90 wt. %. Acrylic acid derivatives which may be used are, for example, acrylic acid esters, acrylic anhydrides, acrylic acid chlorides and/or acrylamides. The carboxyl function may be released (deprotection) by subsequent saponification.

The reaction with ω-halocarboxylic acid salts proceeds at 0°–60° C., preferably 10°–60° C., and is described in the literature reference R. Hering, *Chelatbildende Ionenaustauscher* (Akademie-Verlag, Berlin, 1967) for the synthesis of so-called "chelate ion exchangers". Usual ω-halocarboxylic acid salts are sodium 2-chloroacetate and sodium 3-chloropropionate and higher homologs.

The polyamine/polycarboxylic acid resins according to the invention surprisingly exhibit only very slight changes in volume on conversion from the Na form to the catalytically active H form and vice versa.

The acrolein is hydrated by introducing acrolein and water into the hydration stage in a weight ratio of 1:2 to 1:20, in particular of 1:3 to 1:10 and preferably of 1:3 to 1:6. The reaction to yield 3-hydroxypropionaldehyde proceeds within the temperature range from 30° to 120° C. A temperature in the range from 40° to 90° C. is preferred. Hydration particularly preferably proceeds at 50° to 80° C. A temperature of below 40° C. generally results in excessively long reaction times. A temperature of above 90° C. results in reduced selectivity and problems with regard to the service life of the exchange resins.

In the temperature range below the boiling point of acrolein, the reaction may proceed at standard pressure or moderate pressure. At reaction temperatures of about or above the boiling point of acrolein, the reaction will be performed at a pressure in the range from approximately 2 to 20 bar. In the preferred temperature range of 40° to 90° C., pressure in the range from 2 to 5 bar has proved suitable.

Hydration is generally performed up to an acrolein conversion in the range from 30 to 90% or above. Conversion of 40 to 90% and in particular of 50 to 80% is preferred.

Polymerization inhibitors, such as for example hydroquinone, hydroquinone monomethyl ether or butylated phenols, may conveniently be added to the acrolein/water mixture in a quantity of 100 to 2000 ppm.

Hydration may be performed batch-wise or continuously in per se known reactors, such as for example stirred reactors, loop reactors, suspended bed, fluidized bed or fixed bed reactors. The last-stated reactors are preferred to the loop and stirred reactors. The flow rate through a fixed bed reactor, which contains the ion exchangers and is provided with a heatable jacket, and the reaction temperature will be adjusted relative to each other in such a manner that the desired acrolein conversion is achieved in a single pass of the reaction mixture through the reactor.

Once the ion exchanger has been separated, which may proceed conventionally by settling or filtration or occurs by itself if a resin bed is used, unreacted acrolein is, if necessary, removed from the reaction mixture. The acrolein may be separated in a known manner, in particular by distillation, preferably under reduced pressure and at temperatures of below 80° C. The recovered acrolein, optionally after stabilization, may be returned to the process. The resultant, virtually acrolein-free hydroxy-propionaldehyde solution may be reconcentrated, for example with a film evaporator, before hydrogenation.

Catalytic hydrogenation of the 3-hydroxypropionaldehyde in the liquid phase is performed in a manner known per se and in conventional hydrogenation apparatus. The catalyst may be used either in suspended form as such or may be applied to a support or may be located in a fixed bed reactor. Homogeneous catalysts may also be used. Particularly suitable suspended catalysts are Raney nickel, which may be doped with various other metals, and finely divided platinum on a support, such as for example, activated carbon. Fixed bed catalysts may be the substances stated in U.S. Pat. No. 2,434,110. Nickel catalysts have proved to be particularly effective catalysts. Hydrogenation is performed under pressure and at elevated temperature in order to achieve a high conversion rate, wherein the aqueous solution has a pH value in the range from 3.0 to 8.5, preferably about 6. Pressures of 20 to 250 bar, in particular 40 to 140 bar, and temperatures of 40° to 140° C., in particular 60° to 100° C., are preferred.

The 3-hydroxypropionaldehyde may also be hydrogenated in the gas phase, as described, for example, in DE-PS 20 54 601.

The present invention also provides an ion exchanger which is characterized in that a polyamine-resin based on a crosslinked polyacrylamide matrix has been reacted with acrylic acid, acrylic acid derivatives or the salt of an ω-haloalkanoic acid.

Advantages of the hydration catalysts or ion exchangers produced and used according to the invention are:

1. Very small changes in volume on conversion of the resins according to the invention from the sodium form into the H form ("activation") with dilute acid, in comparison with known chelating ion exchangers of the iminocarboxylic or aminomethylphosphonic acid type.
2. The polyamine structure of the catalyst precursor allows efficient derivatization with an elevated carboxylic acid group density, which is characterized by the achievable total capacity of the resultant resins in the range from 0.5–8.0 meq $H^+$/ml, preferably of 1.0–5.0 meq $H^+$/ml. In contrast, when monoamine precursors (for example, aminomethylated polystyrene/divinylbenzene resin) are used, the achievable total capacity is limited due to their monofunctionality.
3. In comparison with other ion exchangers, the ion exchange catalysts according to the invention exhibit greater activity and selectivity in the hydration of acrolein to 3-hydroxypropionaldehyde (see Examples).

DETAILED DESCRIPTION OF THE PREFERRED EMBODIMENTS

EXAMPLES

Example 1

300 g of the polyamine resin E304/88 (Bayer AG) are refluxed in 1 liter of 1,4-dioxane. The pre-swollen resin is separated by vacuum filtration and washed with distilled water. A 1 liter autoclave is filled with 300 g of freshly distilled, stabilized acrylic acid, 200 g of water and the resin, sealed and repeatedly purged with nitrogen to a pressure of 15 bar. The resin is then heated in the autoclave to 70° C. for 3 hours and to 130° C. for a further 2 hours. The resin is separated by vacuum filtration, washed with water and treated with dilute hydrochloric acid (5 wt. %) to activate it.

The resultant resin has a total capacity (TC) of 1.8 meq $H^+$/ml and exhibits no change in volume on activation.

Example 2

200 g of the polyamine resin E304/88 (Bayer AG) are repeatedly washed with distilled water and separated by vacuum filtration. 200 g of the washed resin, 300 g of freshly distilled acrylic acid and 200 g of water in a 2 liter, 3-necked flask are heated for 6 hours to 65–68° C. with gentle stirring. The resin is then separated by vacuum filtration, washed with distilled water and treated with dilute hydrochloric acid (5 wt. %) to activate it.

The resultant resin has a total capacity (TC) of 2.7 meq $H^+$/ml and exhibits no change in volume on activation.

Example 3

100.5 g (0.64 mol) of 3-bromopropionic acid are added in portions with ice-cooling to an aqueous solution prepared from 35 g (0.33 mol) of sodium carbonate and 165 g of water. The resultant mixture is combined with ice-cooling with 50 g of the washed-polyamine resin E304/88 (Bayer AG) and stirred for 6 hours while rising slowly to room temperature. Stirring is then continued for approximately 2 hours at 40–60° C. The pH value of the reaction mixture is held constant within the range from 8–10 during the reaction by continuous or portion-wise addition of sodium carbonate solution. Once the reaction is complete, the resin is washed until free of alkali with completely deionized water and treated with dilute hydrochloric acid (5 wt. %) or sulfuric acid (2 N) to activate it.

The resultant resin has a total capacity (TC) of 3.21 meq $H^+$/ml and exhibits an approximately −5% change in volume on conversion into the catalytically active H form (activation).

Elemental analysis of the starting resin and of the resultant polyamine/polycarboxylic acid resins (Examples 1–3) reveals the following results (Table 1):

TABLE 1

| Ion exchange resin | Drying loss[a] (3 h, 110° C., 1 mbar) (%) | C (%) | H (%) | N (%) | O (%) | S (%) | Total (%) | O/N ratio |
|---|---|---|---|---|---|---|---|---|
| Lewatit E304/88 (OH form) (anion exchanger) | 55.4 | 54.4 | 9.2 | 21.8 | 14.5 | — | 99.9 | 0.58 |
| Lewatit E304/88, washed (OH form) (anion exchanger) | 57.0 | 54.2 | 9.2 | 21.3 | 14.8 | — | 99.5 | 0.61 |
| Example 1 (H form) (cation exchanger) | 46.8 | 54.3 | 7.8 | 13.7 | 23.9 | — | 99.7 | 1.53 |
| Example 2 (H form) (cation exchanger) | 45.4 | 52.0 | 7.9 | 12.5 | 26.8 | — | 99.2 | 1.88 |
| Example 3 (H form) (cation exchanger) | 29.7 | 43.2 | 7.3 | 11.1 | 33.0 | 4.4[b] | 99.0 | 2.60 |

[a] Elemental analysis was performed after determination of drying loss (3 hours' storage at 110° C./1 mbar).
[b] Exchanger Ek 3/96 was activated with 2N $H_2SO_4$.

In comparison with the starting material (E304/88), the resins according to the invention of Examples 1–3 have an increased oxygen content. The increase in the O/N ratio from 0.6 in E304/88 to 1.5–2.6 (Examples 1–3) reflects the derivatization with acid functions (carboxyl groups). The analytical results thus substantiate the chemical modification of the starting resin.

Screen analysis of the ion exchanger samples shows that the grain size and grain size distribution are not changed by derivatization: the grain size range (at least 90%) for E304/88 and Examples 1–3 is 0.35–1.40 mm. The effective grain size (median value) is 0.77±0.05 mm.

Hydration of Acrolein

Examples 4–6 and Comparative Examples (CE 1–4)

The following test is performed to determine the activity of the prior art ion exchangers (Comparative Examples CE 1 to CE 3) and the ion exchangers according to the invention (Examples 1 to 3):

A 20 ml septum vial is filled with 10 ml of ion exchange catalyst. 14 ml of an aqueous acrolein solution containing 19–20 wt. % acrolein are added. The mixture is shaken with a rotary motion for 3 minutes at room temperature and the actual acrolein concentration of a sample is determined by HPLC. The septum vial is stirred for the stated time in a water bath at the stated temperature according to Table 1 and the reaction contents then analyzed. Table 2 shows the acrolein conversion and the selectivity for 3-hydroxypropionaldehyde after 30 and 60 minutes' reaction, the initial acrolein concentration and the reaction temperature.

A strongly acidic ion exchanger (CE 1) gives rise to elevated acrolein conversion, but inadequate selectivity. Only moderate selectivity at low conversion is achieved with the weakly acidic, non-chelating ion exchanger (CE 2). A weakly acidic, $Ca^{2+}$ doped ion exchanger is more reactive, but also only moderately selective (CE 3). The nonderivatized polyamine resin (CE 4), as mentioned in Examples 1–3, is unsuitable and, as a result of its basicity (OH form), results in rapid polymerization of the acrolein (very low selectivity). In contrast, the polyamine/polycarboxylic acid ion exchangers according to the invention (Examples 4–6) are not only very active but also very selective. The slight decrease in selectivity even at high conversions (>80%) is striking.

Example 7

Acrolein is continuously hydrated over an extended period in a laboratory fixed bed reactor containing the ion exchange resin from Example 2. Conversion and selectivity are determined by analysis of the product solution. The apparatus consists of a graduated, coolable 2 liter glass vessel for the aqueous acrolein starting solution, an HPLC pump to convey the reaction mixture, a temperature controlled, pressure-resistant, precision-ground glass tube (1050 mm×11.3 mm internal diameter), which accommodates the ion exchange packing and is sealed at both ends with adjustable screw fittings, a pressurizing valve, and a 2 liter glass receiver, cooled to +5° C., for the product solution and the necessary temperature control apparatus.

The acrolein/water mixture is cooled to +5° C., introduced and pumped by means of the HPLC pump at a constant rate through the fixed bed of 100 ml of ion exchange resin maintained at the reaction temperature. After a start up period of 3–5 hours to establish steady-state conditions, the initial mixture is replaced and then pumped through the temperature-controlled glass tube under constant test conditions for a period of some hours. This measurement is repeated several times. The product solutions obtained in each case (HPA/Ae) are analyzed by HPLC (see Table 3).

TABLE 2

| | Catalyst name | Functional group | Initial acrolein conc. (wt. %) | Temperature (°C.) | Conversion (%) (after 0.5 h) (after 1 h) | Selectivity (%) (after 0.5 h) (after 1 h) |
|---|---|---|---|---|---|---|
| CE 1 | ® Lewatit S 100, * H form | —$SO_3H$ sulfonic acid | 19.9 | 70 | 92 (1.0 h) | 22 (1.0 h) |
| CE 2 | ® Lewatit CNP 80, * H form | —COOH | 15.1 | 60 | 22 (1.0 h) | 49 (1.0 h) |
| CE 3 | ® Lewatit CNP LFWS, *H form, $Ca^{2+}$ doped | —COOH/(—COO)$_2$Ca | 15.7 | 70 | 43 (1.0 h) | 50 (1.0 h) |
| CE 4 | ® Lewatit E304/88, **OH form | polyamine | 16.0 | 50 | 50 (0.5 h) 80 (1.0 h) | 10 (0.5 h) 5 (1.0 h) |
| Example 4 | Cation exchanger from Example 1 H form | polyamine/ polycarboxylic acid | 15.9 | 50 | 62 (0.5 h) 84 (1.0 h) | 86 (0.5 h) 85 (1.0 h) |
| Example 5 | Cation exchanger from Example 2 H form | polyamine/ polycarboxylic acid | 16.5 | 50 | 60 (0.5 h) 84 (1.0 h) | 90 (0.5 h) 87 (1.0 h) |
| Example 6 | Cation exchanger from Example 3 H form | polyamine/ polycarboxylic acid | 16.6 | 50 | 85 (0.5 h) 93 (1.0 h) | 80 (0.5 h) 75 (1.0 h) |

*Bayer AG
**application product, Bayer AG

Used Ion Exchange Polyamine/polycarboxylic Acid Resin from Example 2
Initial acrolein concentration: 18.0 wt. %,
LHSV (=liquid hourly space velocity): 0.65 h$^{-1}$

TABLE 3

| Operating time (hours) | Temperature (°C.) | Conversion (%) | Selectivity (%) |
|---|---|---|---|
| 40 | 45 | 36 | 90 |
| 60 | 50 | 50 | 89 |
| 120 | 60 | 60 | 85 |

Example 8

Hydrogenation of an aqueous solution of 3-hydroxypropionaldehyde (HPA) obtained according to Example 7 with Raney nickel.

Unreacted acrolein, together with a proportion of the water is removed from the reaction solution from Example 7 in a continuously operated distillation column with a film evaporator at approximately 400 mbar. 500 g of the resultant solution are hydrogenated within 60 minutes at pH 6–7 in a 1000 ml autoclave with a sparging agitator at a hydrogen pressure of 135 bar, a temperature of 75° C.–140° C. and a stirrer speed at 1000 rpm in the presence of 5.8 g of Raney nickel. HPA conversion is 99.9% and the 1,3-propanediol yield, relative to the introduced acrolein, is 85%. The reaction solution is worked up in a known manner by distillation.

What is claimed is:

1. A process for the production of 1,3-propanediol by hydrating acrolein in the presence of an ion exchanger to form 3-hydroxypropionaldehyde, comprising:

reacting acrolein and water in a ratio by weight of 1:2 to 1:20 at 30° to 120° C. and a pressure in a range from 1 to 20 bar, in the presence of an ion exchange hydration catalyst;

separating the ion exchanger and any unreacted acrolein from the reaction mixture, and then catalytically hydrogenating the 3-hydroxypropionaldehyde in liquid or gas phase using hydrogenation catalysts, wherein the ion exchanger hydration catalyst comprises polyamine/polycarboxylic acid resins produced by reacting polyamine resins based on a crosslinked polyacrylamide matrix with acrylic acid, acrylic acid derivatives or a salt of an ω-haloalkanoic acid.

2. An ion exchanger comprising reaction product derived from a polyamine resin and a carboxylic acid wherein said polyamine resin is based on a crosslinked polyacrylamide matrix and said carboxylic acid is selected from the group consisting of acrylic acid, acrylic acid derivatives and ω-haloalkanoic acid salt.

3. An ion exchange according to claim 2 wherein said carboxylic acid is acrylic acid.

4. An ion exchange according to claim 2 wherein said carboxylic acid is an acrylic acid derivative.

5. An ion exchange according to claim 2 wherein said carboxylic acid is a ω-haloalkanoic acid salt.

* * * * *